US005510325A

United States Patent [19]

Ehret et al.

[11] Patent Number: 5,510,325

[45] Date of Patent: Apr. 23, 1996

[54] ESSENTIAL OIL

[75] Inventors: Charles Ehret; Martin Petrzilka, both of Wetzikon, Switzerland

[73] Assignee: Givaudan-Roure Corporation, Clifton, N.J.

[21] Appl. No.: 400,489

[22] Filed: Mar. 8, 1995

Related U.S. Application Data

[63] Continuation of Ser. No. 185,992, filed as PCT/EP93/01195, May 13, 1993, abandoned.

[30] Foreign Application Priority Data

May 20, 1992 [EP] European Pat. Off. .............. 92108469

[51] Int. Cl.$^6$ .................................................... A61K 7/46

[52] U.S. Cl. ................................................ 512/5; 426/542

[58] Field of Search ................................ 512/5; 426/542

[56] References Cited

U.S. PATENT DOCUMENTS 3,415,813 12/1968 Thomas et al. ............................ 512/1

FOREIGN PATENT DOCUMENTS 202647 5/1986 European Pat. Off. .

468189 6/1991 European Pat. Off. .

OTHER PUBLICATIONS

Abstract of Japanese Patent No. 57200321.

P. Vigne, Parfums, Cosmetiques, Aromes (78), pp. 97–105 (1987).

D. J. Cram and G. S. Hammond, Organic Chemistry, pp. 299–300 (1964).

R. F. Fieser and M. Fieser, Reagents for Organic Synthesis, pp. 599–603 (1967).

R. F. Fieser & M. Fieser, Reagents for Organic Synthesis, pp. 1049–1055 (1967).

R. Ter Heide et al, Qualitative Analysis of the Odoriferous Fraction of Oakness, J. Agric. Food Chem., vol. 23, No. 5 (1975).

R. C. Larock, Comprehensive Organic Transformations, A Guide to Functional Group Preparations, pp. 527–535 (1989).

*Primary Examiner*—James H. Reamer

*Attorney, Agent, or Firm*—George M. Gould; George W. Johnston; Mark E. Waddell

[57] ABSTRACT

A process for the preparation of hypoallergenic moss oils, comprising reacting the starting moss oil, a concrete or preferably an absolute thereof, with an aldehyde reducing agent, in an organic solvent medium.

18 Claims, No Drawings

ESSENTIAL OIL

This is a continuation of U.S. application Ser. No. 08/185,992, filed Jan. 14, 1994, now abandoned which is a 371 of PCT/EP93/01195 filed May 13, 1993.

BACKGROUND

The present invention relates to the preparation of moss oils which are characterized by hypoallergenicity, i.e. by a strongly reduced allergenic potential and excellent olfactive performance in perfume compositions.

DETAILED DESCRIPTION.

Moss oils are highly appreciated by perfumers for their typical woody notes and play an important role in the creation of perfumes, e.g. of the so-called "Chypre" or "Fougère" type. They are obtained by solvent extraction of lichens including, in particular *Evernia prunastri* L. for the Oakmoss oil and *Evernia furfuracea* L. for Treemoss oil. The total mount of lichens treated worldwide for perfumery use may be estimated to 6000 tons/year (P. Vigne, Parfums, Cosmetiques, Arômes, (78), p 97–105, 1987) and represents an estimated annual turnover dose to $ 35 millions.

Moss extracts, e.g. moss absolutes or concretes, which are the most frequently used moss oil products have been reported to cause contact sensitization on human skin, and several groups of researchers have shown that some components of moss oils, particularly ethyl hematommate I, ethyl chlorohematommate II, atranorin III and chloroatranorin IV as depicted on page 3 are involved in these allergenic reactions.

European patent publication No. 202,647 (Shiseido Company Ltd.) describes a process for the preparation of hypoallergenic moss oils by removing allergenic substances from moss oils by chromatography, solvent extraction, countercurrent partition and membrane separation followed by a catalytic hydrogenation and/or an alkaline treatment. The allergens removed in this way are aldehydes which include the above mentioned ethyl hematommate I, ethyl chlorohematommate II, atranorin III and chloroatranorin IV.

The more recent European patent publication No. 468,189 (Roure S. A.) describes a process for the preparation of hypoallergenic moss oils by reacting, e.g. moss absolutes or concretes in alcoholic solution with amino add(s) under mono-phasic conditions followed by removal of the insolubilized allergenic substances I–VI.

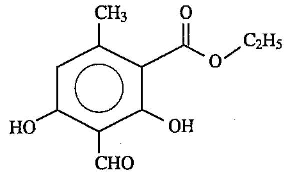

I

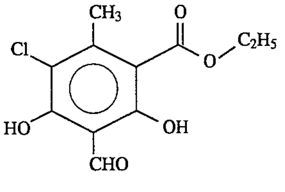

II

-continued

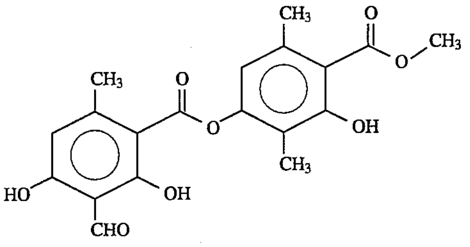

III

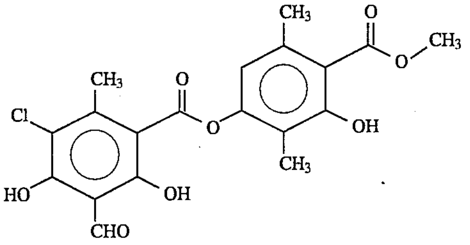

IV

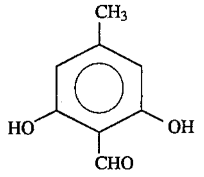

V

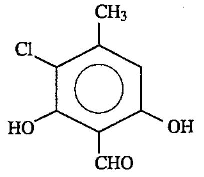

VI

The concentrations of the allergens I–VI achieved in this way are dearly below the critical levels (0.05–1%) established experimentally via allergenicity tests.

The goal of the present invention was to eliminate now substantially further the above-mentioned aldehydes I–VI by using an economical process without affecting significantly the original color and olfactive performance of the starting moss oil, thereby providing moss absolutes or concretes with a strongly reduced allergenic potential. It was achieved by reacting moss extracts e.g. concretes or absolutes with appropriate reducing agents, e.g. alkali metal borohydrides, which specifically and exclusively reduce the allergenic aldehydes I–VI to the corresponding primary alcohols.

A further advantage of the novel process consists in the avoidance of concomitant formation of trace amounts of colorants, which can cause inconveniences for some perfumery applications.

The present invention describes thus the reaction between moss extracts, e.g. oils, concretes or absolutes, with appropriate aldehyde reducing agents, e.g. complex metal hydrides, and preferably with alkali metal borohydrides, e.g. lithium or sodium borohydride, in o organic solvent systems.

The starting moss extracts subjected to this treatment are suitably obtained by solvent extraction of lichens and include in particular the Oakmoss concrete (*Evernia prunastri* L.) and the Treemoss concrete (*Evernia furfuracea* L.) and, preferably, the absolutes thereof.

It is known from the literature [e.g. Reagents for Organic Synthesis, L. F. Fieser and M. Fieser, p 599–603 and 1049–1055, Editor John Wiley and Sons, Inc., 1967]that complex alkali metal hydrides, e.g. borohydrides or aluminium hydrides are able to reduce o aldehydes, ketones and even esters. The aldehydic allergens I–VI contribute insignificantly to the total odour of moss extracts, but numerous esters, other aldehydes and ketones are known to be olfactively important minor or major constituents of these extracts [R. Ter Heide et al., Qualitative Analysis of the Odoriferous Fraction of Oakmoss (*Evernia prunastri* (L.) Ach.), J. Agric. Food Chem., 23 (5) p 950–957 (1975)].

It was therefore surprising to find, that the novel process allowed the selective reduction of allergens I–VI without organoleptically deteriorating the moss oil, or in other words, none of the above-mentioned organoleptically active constituents, e.g. no organoleptically relevant esters appear to have been removed from the original moss extract, as was demonstrated by GC data. In addition, the concentration levels found for I–VI are far below the required limits (cf. Table 1) and those achieved in earlier publications [EP publication No. 468,189 and C. Ehret, P. Maupetit, M. Petrzilka, G. Klecak, Int. J. of Cosm. Science, 14, 121–130 (1992)]. Finally, the colors of the resulting non-allergenic moss oils are very dose to the original ones and are therefore suitable for most perfumery applications.

TABLE 1

| Aldehydes | Concentration levels required for moss absolute with reduced allergenic potential (%) |
|---|---|
| Ethyl hematommate I | ≦1 |
| Ethyl chlorohematommate II | ≦0.05 |
| Atranorins III + IV | ≦0.15 |
| Atranol V | ≦0.2 |
| Chloratranol VI | ≦0.2 |

In the broadest context of the present invention, the allergenic moss oil is dissolved in an appropriate organic solvent and treated with preferably an excess of an appropriate aldehyde reducing reagent. The suitable reducing agents are those which are able to o reduce exclusively, or at least preferentially the aldehydes over the esters and belong to various types (cf. R. C. Larock, Comprehensive Organic Transformations, A Guide to Functional Group Preparations, published by VCH Publishers, Inc., New-York, 527–535 [1989],) e.g.:

complex metal or ammonium hydrides, such as sodium, lithium, potassium, zinc, tetraethylammonium borohydrides, etc., substituted complex metal or ammonium hydrides, such as sodium triacetoxyborohydride, potassium triacetoxyborohydride, sodium cyanoborohydride or tetra-n-butylammonium triacetoxyborohydride, metal hydrides, such as diborane or an alkali or aluminium hydride, etc.

The preferred reducing agents are lithium borohydride and sodium borohydride.

The reduction can be carried out according to know methods. It is usually carried out in an organic medium, e.g. in solution using optionally halogenated, aliphatic or aromatic hydrocarbon solvents, such as hexane, cyclohexane or toluene, etc., ester solvents such as ethyl acetate, isopropyl acetate etc., or alcoholic solvents, such as methanol, ethanol etc. Alternatively ether solvents such as t-butyl methyl ether, tetrahydrofuran etc., or halogenated solvents such as methylene chloride may also be used. Another possibility consists in using mixtures of the above-mentioned solvents.

The concentrations of moss extracts applied in the reaction may vary between ca. 5–50%, preferably between ca. 5–15% (w/w).

Convenient amounts of reducing agents, e.g. alkali metal borohydrides, are ca. 0.02–0.1g, preferably ca. 0.03–0.07g per g of moss extract. This amount represents a ca. 2 to 5 fold molar excess, i.e. a ca. 8 to 20 fold reducing equivalent excess.

The reaction temperature is ca. 20°–80° C., preferably ca. 20°–30° C., if, e.g. lithium borohydride is used, and preferably reflux temperature, e.g. that of an alcanol, e.g. ethanol, if sodium borohydride is used.

The reaction is usually quenched after ca. 30 minutes to 3 hours, preferably after ca. 30 to 60 minutes, if sodium borohydride is used, and after ca. 1–2 hours, if lithium borohydride is used.

If water insoluble solvents are used for the reaction, such as hydrocarbons, esters, halogenated and aliphatic ether solvents, work up consists in extensively washing the reaction mixture with water or aqueous acids (e.g. 1–10%, preferably 1–3% aq. HCl solution) followed by water until neutral. Finally the organic solvent is distilled off at reduced pressure without exceeding a temperature of ca. 85° C. Alternatively, if water soluble solvents are used, e.g. an alcohol or a cyclic ether, such as tetrahydrofuran, the solvent is first removed by distillation at reduced pressure. The remaining residue is then redissolved in a water insoluble solvent, e.g. the solvents mentioned above, and worked up as in the previous case.

EXAMPLES

1) Allergenicity

The strongly reduced allergenic potential in the product was in each case determined by conventional, fully established skin sensitization and skin response methods, i.e. in concrete the so-called

* Modified BUEHLER method using guinea pigs, and the
* RIPT (Repeated Insult Patch Test) using human subjects.

2) Analysis

Content of aldehydes I, II, V and VI

The contents of products I, II, V and VI are suitably determined by GC analysis, using an internal standard and working under the following conditions:

* Column: 50m×0.32mm inner diameter, fused silica
* Stationary phase: CP Sil 5CB (a silicone)
* Detector: FID (flame ionisation detector)
* Vector gas: Helium, 2 ml/mm
* Temperature program: 100°–240° C., 2° C./min.
* Internal standard: methyl 2,4-dihydroxy-3,6-dimethylbenzoate Content of aldehydes III and IV The contents of aldehydes Ill and IV are suitably determined by HPLC, using an external standard and working under the following conditions:

* Column: 250 mm length, 4.6 mm i.d.
* Stationary phase: RP 18 (reverse phase, particle size: 7 μm)
* Detector: UV at 260 nm
* Mobile phase A: $H_2O$ acidified to pH 2.8 with conc. $H_3PO_4$ B: acetronitrile

| *Gradient: | | | |
|---|---|---|---|
| Time (min.) | % A | % B | Flow (ml/min.) |
| 0 | 80 | 20 | 1 |
| 30 | 5 | 95 | 1 |
| 40 | 5 | 95 | 1 |

This gradient allows the effective separation of the above nonvolative aldehydes III and IV.

EXAMPLE 1

Production of Oakmoss absolute with strongly reduced allergenic potential using lithium borohydride A 500 ml three-necked flask equipped with a mechanical stirrer, a condenser and a dropping funnel was charged with 15 g of a commercially available melted Oakmoss absolute (Givaudan-Roure, mp about 70° C.), which then was dissolved in 200 ml of cyclohexane/isopropyl acetate 3:1 at room temperature and under $N_2$. To this homogeneous solution was then added dropwise a suspension of 480 mg (22 retool) of lithium borohydride in 100 ml of cyclohexane/isopropyl acetate 3:1 during ca. 30 minutes. Immediately after addition a precipitation occurred and a slight increase of the temperature of the reaction mixture (ca. 6° C.) was observed. After stirring the reaction mixture for an additional 2 hours at room temperature, it was carefully quenched with 150 ml of 0.5% (w/w) aqueous HCl and extracted with cyclohexane/isopropylacetate 3:1 (3×300 ml). The organic layers were washed with water (1×150ml), combined and concentrated at reduced pressure (20 mbars) on a water bath without exceeding a temperature of ca. 85° C. An Oakmoss absolute (12.78 g, 85.2% yield) was obtained in this way, which according to GC- and HPLC-analysis contained extremely small amounts of aldehydes I–VI (cf. Table 2).

TABLE 2

| Aldehyde | Starting Oakmoss absolute (%) | Resulting Oakmoss absolute (%) |
|---|---|---|
| Ethyl hematommate I | 2.40 | <0.01 |
| Ethyl chlorohematommate II | 1.44 | <0.01 |
| Atranorins III + IV | 0.58 | 0.05 |
| Atranol V | 4.24 | 0.06 |
| Chloratranol VI | 2.28 | <0.01 |

EXAMPLE 2

Production of Oakmoss absolute with strongly reduced allergenic potential using sodium borohydride A 250 ml three-necked flask equipped with a mechanical stirrer, a condenser and a dropping funnel was charged with 14.9 g of a commercially available melted Oakmoss absolute (Givaudan-Roure, mp about 70° C.), which then was dissolved in 90 ml of ethanol 96% at room temperature and under $N_2$. To this solution was then added dropwise a suspension of 1 g (26.4 retool) of sodium borohydride in 60 ml of ethanol 96% during ca. 5 minutes. During the addition a slight increase of the temperature (ca. 12° C.) was observed. After stirring the reaction mixture at reflux temperature during 45 minutes, the ethanol was distilled off at reduced pressure (20 mbars) and the residue was taken up in 300 ml of t-butyl methyl ether (TBME). The reaction mixture was then carefully quenched with 150 ml of water and extracted with TBME (3×300ml). The organic layers were washed with water (1×150ml), combined and concentrated at reduced pressure (20 mbars) on a water bath without exceeding a temperature of ca. 65° C. An Oakmoss absolute (12.78 g, 85.2% yield) was obtained in this way, which according to GC- and HPLC- analysis contained extremely small amounts of aldehydes I–VI (cf. Table 3).

TABLE 3

| Aldehyde | Starting Oakmoss absolute (%) | Resulting Oakmoss absolute (%) |
|---|---|---|
| Ethyl hematommate I | 3.78 | 0.11 |
| Ethyl chlorohematommate II | 1.46 | 0.02 |
| Atranorins III + IV | 1.16 | 0.01 |
| Atranol V | 3.30 | <0.01 |
| Chloratranol VI | 1.92 | 0.03 |

EXAMPLE 3

Production of Oakmoss absolute with strongly reduced allergenic potential using sodium borohydride (acidic work up)

A 250 ml three-necked flask equipped with a mechanical stirrer, a condenser and a dropping funnel was charged with 15 g of a commercially available (Givaudan-Roure), melted Oakmoss absolute (mp about 70° C.), which then was dissolved in 100 ml of ethanol 96% at room temperature and under $N_2$. To this solution was then added dropwise a suspension of 1 g (26.4 mmol) of sodium borohydride in 60 ml of EtOH 96% during ca. 5 minutes. During the addition a slight increase of the temperature (ca. 15° C.) was observed. After stirring the reaction mixture at reflux temperature during 45 minutes ethanol was distilled off at reduced pressure (20 mbars) and the residue was taken up in 300 ml of t-butyl methyl ether. The reaction mixture was then carefully quenched with 100 ml of water and acidified to pH=1.5 with ca. 15 ml of 6% aqueous HCl. The organic layer was washed with water (1×150 ml) and concentrated at reduced pressure (20 mbars) on a water bath without exceeding a temperature of ca. 65° C. An Oakmoss absolute (14.42 g, 96.1% yield) was obtained in this way, which according to GC- and HPLC- analysis contained extremely small amounts of aldehydes I–VI (cf. Table 4).

TABLE 4

| Aldehyde | Starting Oakmoss absolute (%) | Resulting Oakmoss absolute (%) |
|---|---|---|
| Ethyl hematommate I | 3.78 | 0.05 |
| Ethyl chlorohematommate II | 1.46 | 0.02 |
| Atranorins III + IV | 1.16 | 0.05 |
| Atranol V | 3.30 | <0.01 |
| Chloratranol VI | 1.92 | <0.01 |

We claim:

1. A process for the preparation of hypoallergenic moss oils, comprising reacting:

(1) a starting material selected from the group consisting of moss oils, concretes, or absolutes thereof, the starting material containing at least one aldehyde allergen, with (2) an aldehyde reducing agent selected from the group consisting of alkali metal hydrides, complex metal hydrides, substituted complex metal hydrides, ammonium hydrides, and substituted ammonium hydrides, in an organic solvent selected from the group consisting of non-halogenated aliphatic hydrocarbons, halogenated aliphatic hydrocarbons, non-halogenated aromatic hydrocarbons, halogenated aromatic hydrocarbons, esters, alcohols, ethers, and mixtures thereof, under conditions such that allergenic aldehydes are reduced to non-allergenic alcohols.

2. The process of claim 1 wherein the aldehyde reducing agent is an alkali metal borohydride.

3. The process of claim 2 wherein the aldehyde reducing agent is selected from sodium borohydride and lithium borohydride.

4. The process of claim 3, wherein the aldehyde reducing agent is lithium borohydride and the reaction is carried out at a temperature of from about 20° C. to about 30° C.

5. The process of claim 3, wherein the aldehyde reducing agent is sodium borohydride and the reaction is carried out at a temperature of from about 60° C. to about 80° C.

6. The process of claim 1, wherein the organic solvent is substantially water insoluble.

7. The process of claim 6, wherein the organic solvent is a mixture comprising an aliphatic hydrocarbon and a second component selected from the group consisting of alkane carboxylic acid esters and aliphatic ethers.

8. The process of claim 7, wherein the aliphatic hydrocarbon is selected from hexane, cyclohexane, and mixtures thereof, the alkane carboxylic acid ester is selected from ethyl acetate, isopropyl acetate, and mixtures thereof, and the aliphatic ether is t-butyl ether.

9. The process of claim 1, wherein the organic solvent is water soluble.

10. The process of claim 9, wherein the organic solvent is selected from the group consisting of alkanols and cyclic ethers.

11. The process of claim 10, wherein the organic solvent is selected from ethanol and tetrahydrofuran.

12. The process of claim 9, wherein a work-up is carried out in a water insoluble solvent.

13. The process of claim 12, wherein the work-up is carried out in a water insoluble solvent comprising an aliphatic hydrocarbon and a second component selected from the group consisting of alkane carboxylic acid esters and aliphatic ethers.

14. The process of claim 13, wherein the aliphatic hydrocarbon is selected from hexane, cyclohexane and mixtures thereof, and the alkane carboxylic acid ester is selected from ethyl acetate, isopropyl acetate and mixtures thereof, and the aliphatic ether is t-butyl ether.

15. The process of claim 1, wherein the reaction is carried out at a temperature from about 20° C. to about 80° C.

16. The process of claim 1, wherein the reaction is conducted under an inert gas or a mixture of inert gases.

17. The process of claim 1, wherein the concentration of each aldehyde allergen in the starting material is lowered to small amounts.

18. The process of claim 17, wherein the concentration of each aldehyde allergen in the starting material is lowered to one percent or less.

* * * * *